United States Patent [19]

Cavero et al.

[11] Patent Number: 4,925,837
[45] Date of Patent: May 15, 1990

[54] PHARMACEUTICAL COMPOSITIONS

[75] Inventors: Icilio Cavero, Creteil; Jean-Louis Cazor, Paris; Peter Hicks, Cachan; Salomon Langer, Paris, all of France

[73] Assignee: Synthelabo, Paris, France

[21] Appl. No.: 106,968

[22] Filed: Oct. 13, 1987

Related U.S. Application Data

[63] Continuation of Ser. No. 846,032, Mar. 31, 1986, abandoned, which is a continuation of Ser. No. 817,262, Jan. 9, 1986, abandoned, which is a continuation-in-part of Ser. No. 692,767, Jan. 16, 1985, abandoned.

[30] Foreign Application Priority Data

| Sep. 14, 1984 | [FR] | France | 85 14088 |
| Jan. 18, 1985 | [FR] | France | 85 00678 |
| Feb. 26, 1985 | [FR] | France | 85 02725 |
| Feb. 26, 1985 | [FR] | France | 85 02726 |

[51] Int. Cl.$^5$ ............ A61K 31/44; A61K 31/55; A61K 31/445; A61K 31/505

[52] U.S. Cl. .................. 514/211; 514/218; 514/252; 514/254; 514/260; 514/319; 514/356; 514/523

[58] Field of Search .................. 514/211, 260

[56] References Cited

U.S. PATENT DOCUMENTS 3,562,257  2/1971  Kugita et al. .................. 514/929

FOREIGN PATENT DOCUMENTS

| 744855 | 3/1970 | Belgium | 514/211 |
| 2389613 | 1/1979 | France | 514/260 |
| 2143532 | 2/1985 | United Kingdom | 514/211 |

*Primary Examiner*—Allen J. Robinson
*Attorney, Agent, or Firm*—Wegner & Bretschneider

[57] ABSTRACT

Pharmaceutical compositions containing, by way of active substance, a combination of an alpha-blocker and a calcium antagonist. The composition is useful in treating cardiovascular disorders, especially hypertension.

2 Claims, No Drawings

PHARMACEUTICAL COMPOSITIONS

This application is a continuation of U.S. application Ser. No. 846,032 filed Mar. 31, 1986, which is a continuation of Ser. No. 817,262 filed Jan. 9, 1986, which in turn is a continuation-in-part of Ser. No. 692,767 filed Jan. 16, 1985, all now abandoned.

This application is a continuation of Ser. No. 817,262 filed, Jan. 9, 1986, which in turn is a continuation-in-part of Ser. No. 692,767, filed Jan. 16, 1985, both of which are incorporated herein by reference.

The present invention relates to pharmaceutical compositions containing an alpha-blocker and a calcium antagonist, which pharmaceutical compositions are intended for the treatment of cardiovascular diseases, more especially hypertension of whatever origin and angina pectoris.

The applicants have found that, surprisingly, there is a substantial synergistic effect between the antihypertensive properties of two of these alpha-blocking and calcium-antagonistic compounds when they are combined.

The alpha-blockers possessing antihypertensive properties and which are more especially suitable according to the invention are alfuzosin, prazosin, terazosin, doxazosin, trimazosin, bunazosin, urapidil and indoramin, the formulae 1, 2, 3, 4, 5, 6, 7 and 8 of which are given in Appendix 1.

The calcium antagonists which are suitable according to the invention are diltiazem, nifedipine and verapamil, the formulae 9, 10 and 11 of which are given in Appendix 2.

The pharmaceutical compositions of the invention have been subjected to a series of pharmacological trials which reveal their advantageous properties in the cardiovascular field.

The tests used are as follows:

INTRAVENOUS TEST

SHR rats, over 5 months, are anesthetized with sodium pentobarbital (60 mg/kg i.v.) and prepared so that the blood pressure is measured from a cannulated carotid artery. The products to be tested are administered by intravenous route via the femoral vein.

10 μg/kg/mn of diltiazem or of the solvent are infused by intravenous route (the solvent is distilled water containing 0.09% of NaCl), during 45 mn.

10 mn later, alfuzosin is injected (2 μg/kg/mn during 5 mn). The maximal changes of the blood pressure after injection of diltiazem, alfuzosin or of their association are measured.

Diltiazem alone produces a sustained decrease of blood pressure of 12.6±2.1 mmHg (n=15).

With alfuzosin alone the decrease of blood pressure is of 19.7±4,7 mmHg (n=6) at the end of the administration, and of 4.2±1.5 mmHg, 15 mn later.

With the association diltiazem/alfuzosin the decrease of blood pressure is of 58.4±7.8 mmHg (n=7) at the end of the administration of alfuzosin, and still of 48.7±8.7 mmHg, 15 mn later.

ORAL TEST 1

Male vigile SHR rats, aged of more than 5 months, are used in the oral test.

Their arterial blood pressure and cardiac frequency are measured, continuously, from a catheterized tail artery. When the arterial blood pressure is stabilized (after about 2 hr), the animals receive; by oral route, in a volume of 5 ml/kg, or 1 mg/kg of alfuzosin, or 12.5 mg/kg of diltiazem, or placebo (distilled water+0.2% of Tween 80), or the association diltiazem/alfuzosin.

The oral administration of 12.5 mg/kg of diltiazem has no significant influence on the arterial blood pressure or on the cardiac frequency of the rat.

Alfuzosin (1 mg/kg p.o.) slightly decreases the arterial blood pressure (−22±4 mmHg after 30 mn; the initial blood pressure being 186±4 mmHg; n=9). 1 h after the treatment, the parameter is turned to the initial value.

The association of alfuzosin/diltiazem provokes a decrease of the arterial blood pressure.

The hypotensive activity of the association is maximal 15 mn after the treatment (−96±4 mmHg; initial pressure=195±mmHg; n=11).

1 h after the treatment the decrease is still equal to 70% of the maximum.

4 h after the treatment the decrease is still equal to 30% of the maximum.

The cardiac frequency is not significantly modified by each of the compounds or by the association.

ORAL TEST 2

Spontaneously hypertensive rats ("SHR") over 5 months old are placed for 30 min in an air-conditioned cage maintained at 28° C. The systolic pressure of the rats is measured according to the method described by Gerold and Tschirky (Arzneim, Forsch. 1968, 18, 1285).

To a group of 6 SHR rats, there are administered either a dose of calcium antagonist and a dose of alpha-blocker separately, or the combination of the two alpha-blocking and calcium-antagonistic doses.

The systolic pressure is measured before the administration of the therapeutic agents, and then 3 to 5 hours after the administration of one of the compounds or of the combination of two of the therapeutic agents.

The results are given in the form of decreases in the blood pressure with respect to the original pressure.

The table which follows gives the results obtained for the compounds administered alone and for the combinations of two of the therapeutic agents.

TABLE

| Compound | dose mg/kg p.o. | original pressure (mm Hg) | Decrease in the systolic pressure (mm Hg) |
| --- | --- | --- | --- |
| diltiazem | 12.5 | 222 ± 4 | −1 ± 2 |
| alfuzosin | 1 | 203 ± 4 | −8 ± 3 |
| alfuzosin + diltiazem | 1 + 12.5 | 202 ± 1 | −33 ± 9* |
| prazosin | 0.3 | 215 ± 4 | −26 ± 5 |
| prazosin + diltiazem | 0.3 + 12.5 | 218 ± 6 | −62 ± 5* |
| trimazosin | 3.0 | 210 ± 3 | −3 ± 2 |
| trimazosin + diltiazem | 3.0 + 12.5 | 210 ± 4 | −44 ± 6* |
| terazosin | 0.5 | 208 ± 3 | −28 ± 4 |
| terazosin + diltiazem | 0.5 + 12.5 | 212 ± 5 | −45 ± 6* |
| urapidil | 3.0 | 208 ± 4 | −13 ± 7 |
| uradipil + diltiazem | 3 + 12.5 | 208 ± 3 | −32 ± 2* |
| verapamil | 15 | 217 ± 5 | −28 ± 9 |
| alfuzosin | 1 | 221 ± 2 | −15 ± 5 |
| verapamil + alfuzosin | 15 + 1 | 209 ± 6 | −120 ± 5* |
| nifedipine | 10 | 219 ± 4 | −5 ± 4 |
| alfuzosin | 0.3 | 213 ± 2 | 13 ± 4 |
| alfuzosin | 1 | 216 ± 2 | 18 ± 7 |
| nifedipine + alfuzosin | 10 + 0.3 | 211 ± 3 | −32 ± 2* |

TABLE-continued

| Compound | dose mg/kg p.o. | original pressure (mm Hg) | Decrease in the systolic pressure (mm Hg) |
|---|---|---|---|
| nifedipine + alfuzosin | 10 + 1 | 219 ± 3 | −55 ± 5* |

*Effect significantly greater than the simple addition of the effects of each of the compounds.

These results show that the combination of one of the calcium antagonists chosen according to the invention with one of the above-mentioned alpha-blockers produces an antihypertensive effect which is significantly larger than the sum of the effects brought about by each of the compounds administered in isolation.

There is consequently a synergistic effect between the antihypertensive effects of the calcium antagonist and the alpha-blockers.

The pharmaceutical compositions of the invention contain from 5 to 120 mg of one of the calcium antagonists and from 0.1 to 30 mg of one of the above-mentioned alpha-blockers, per unit dose.

The preferred pharmaceutical compositions of the invention are as follows:
compositions containing diltiazem and alfuzosin,
compositions containing verapamil and alfuzosin,
compositions containing nifedipine and alfuzosin,
compositions containing diltiazem and prazosin,
compositions containing diltiazem and terazosin,
compositions containing diltiazem and doxazosin,
compositions containing diltiazem and trimazosin,
compositions containing diltiazem and bunazosin,
compositions containing diltiazem and urapidil,
compositions containing diltiazem and indoramin.

The pharmaceutical compositions of the invention can take any form suitable for oral or parenteral administration, in combination with any suitable excipient.

The pharmaceutical compositions of the invention can be used for the treatment of hypertension and angina pectoris and for the treatment of other disease such as asthma and urological afflictions.

The daily dosage is such that from 5 to 240 mg of one of the calcium antagonists and from 1 to 50 mg of one of the alpha-blockers are administered.

Appendix 1

Alfuzosin

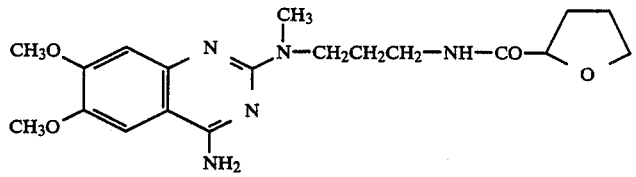

4-amino-6,7-dimethoxyquinazolines

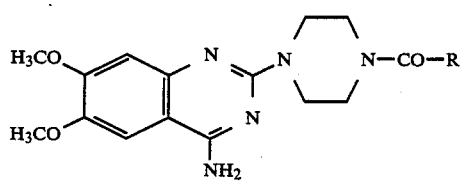

.prazosin  R = 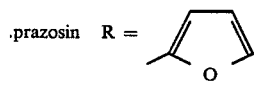  (2)

.terazosin  R = 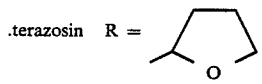  (3)

.doxazosin  R = 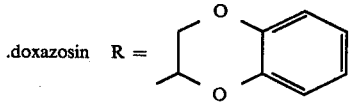  (4)

-trimazosin (5)

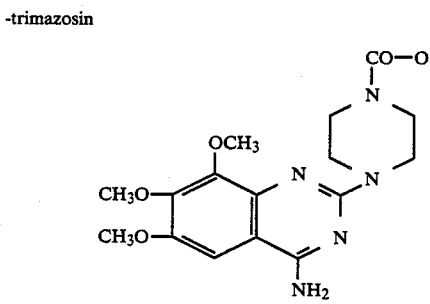

Appendix 1

-bunazosin (6)

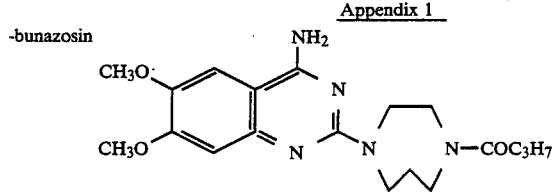

-urapidil (7)

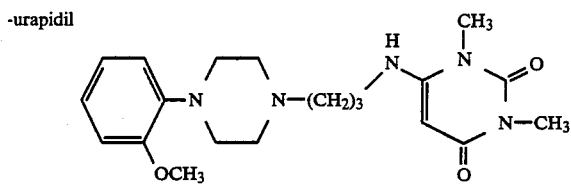

-indoramin (8)

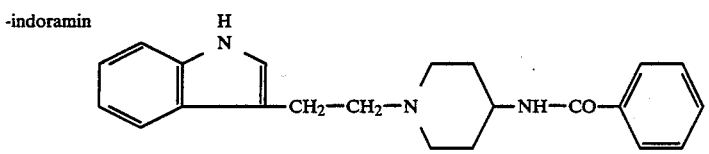

APPENDIX 2

-diltiazem (9)

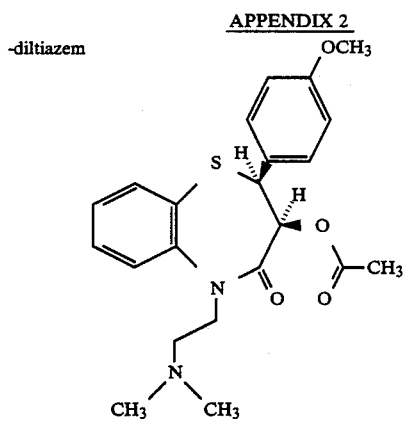

-nifedipine (10)

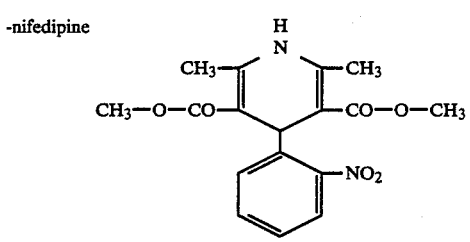

-continued
APPENDIX 2

Verapamil (11)

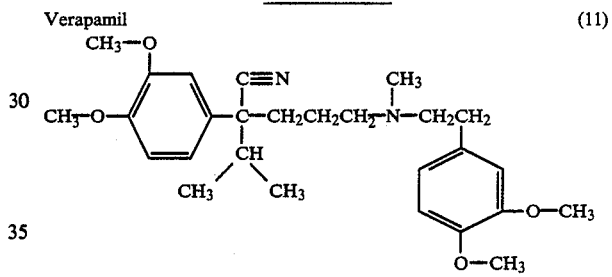

We claim:
1. A pharmaceutical composition comprising a combination of diltiazem and alfuzosin in an amount effective for the treatment of hypertension, the diltiazem being present in the amount of about 25 to 160 mg, the alfuzosin being present in the amount of about 0.1 to 10 mg, the diltiazem and alfuzosin being present in relative amounts such that the anti-hypertensive effect observed upon administration of the combination of diltiazem and alfuzosin is greater than the sum of the individual anti-hypertensive effects that would be observed upon separate administration of the diltiazem and alfuzosin alone, and a pharmaceutically acceptable carrier.

2. A method of treating a subject suffering from hypertension, comprising administering to said subject an anti-hypertensive-effective amount of a combination of diltiazem and alfuzosin, the daily dosage of the diltiazem being about 25 to 240 mg, the daily dosage of the alfuzosin being about 0.2 to 20 mg, the relative amounts of diltiazem and alfuzosin administered being such that the anti-hypertensive effect observed upon administration of the combination of diltiazem and alfuzosin is greater than the sum of the individual anti-hypertensive effects that would be observed upon separate administration of the diltiazem and alfuzosin alone.

* * * * *